US006945996B2

United States Patent
Sedransk

(10) Patent No.: US 6,945,996 B2
(45) Date of Patent: Sep. 20, 2005

(54) REPLACEMENT MITRAL VALVE

(76) Inventor: Kyra L. Sedransk, 15830 S. Park Blvd., Shaker Heights, OH (US) 44120

( * ) Notice: Subject to any disclaimer, the term of this patent is extended or adjusted under 35 U.S.C. 154(b) by 0 days.

(21) Appl. No.: 10/418,483

(22) Filed: Apr. 18, 2003

(65) Prior Publication Data

US 2004/0210303 A1 Oct. 21, 2004

(51) Int. Cl.$^7$ .................................................. A61F 2/24
(52) U.S. Cl. ...................................... 623/2.12; 623/2.13
(58) Field of Search ..................... 623/2.1, 2.12–2.13, 623/2.28, 2.3, 2.41, 2.16

(56) References Cited

U.S. PATENT DOCUMENTS

| 6,312,464 | B1 | * | 11/2001 | Navia ......................... 623/2.12 |
| 6,328,763 | B1 | | 12/2001 | Love et al. ................. 623/2.15 |
| 6,358,277 | B1 | * | 3/2002 | Duran ......................... 623/2.12 |
| 6,440,164 | B1 | | 8/2002 | DiMatteo et al. .......... 623/1.24 |
| 6,673,109 | B2 | * | 1/2004 | Cox ............................. 623/2.12 |
| 2002/0116053 | A1 | * | 8/2002 | Simpson et al. ............ 623/1.26 |
| 2002/0173843 | A1 | * | 11/2002 | Peredo ........................ 623/2.16 |
| 2003/0078653 | A1 | * | 4/2003 | Vesely et al. ............... 623/2.16 |
| 2003/0105519 | A1 | * | 6/2003 | Fasol et al. .................. 623/2.1 |
| 2003/0163194 | A1 | * | 8/2003 | Quijano et al. ............. 623/2.11 |
| 2003/0163195 | A1 | * | 8/2003 | Quijano et al. ............. 623/2.13 |
| 2004/0024452 | A1 | * | 2/2004 | Kruse et al. ................ 623/2.13 |
| 2004/0117009 | A1 | * | 6/2004 | Cali et al. ................... 623/2.12 |
| 2004/0122513 | A1 | * | 6/2004 | Navia et al. ................ 623/2.12 |
| 2004/0143323 | A1 | * | 7/2004 | Chawla ....................... 623/2.12 |

OTHER PUBLICATIONS

Sedransk, et al., "Failure Mechanics of Mitral Valve Chordae Tendineae", J Heart Valve Dis V. 11, No. 5, Sep. 2002, ISSN 0966–8519.

* cited by examiner

*Primary Examiner*—Suzette J-J Gherbi
(74) *Attorney, Agent, or Firm*—Fay, Sharpe, Fagan, Minnich & McKee, LLP

(57) ABSTRACT

A sewing ring (12) has a diameter commensurate with a diameter of a removed mitral valve. Skirts (44, 46) of mesh or net material extend downward from the sewing ring and line the walls of an associated vessel (58). Basal chordae simulating structures (34, 36) in the form of elongated strips of mesh or netting, rods, or the like extend from the skirt to an underside of each of two valve leaflets (14, 16). Marginal chordae simulating structures (30, 32) extend between each leaflet and the basal chordae simulating structure. The sewing ring (12) is stitched to an open end of a vessel and inner ends of the basal chordae simulating structure are stitched or stapled (50, 52) to associated papillary musculature (54, 56). In this manner, the papillary muscles assist in controlling the timing and control of the mitral valve.

13 Claims, 3 Drawing Sheets

REPLACEMENT MITRAL VALVE

BACKGROUND OF THE INVENTION

The present invention relates to replacement valves for the circulatory system. It finds particular application in conjunction with mitral valves for human hearts and will be described with particular reference thereto.

Heretofore, various styles of flow operated check valves have been utilized as replacement heart valves. One prior art heart valve includes a ball and valve seat arrangement which limits blood flow to a single direction. A cage surrounding the ball and attached to a sewing ring around the valve seat limits movement of the ball away from the valve seat and natural blood flow.

In another prior design, a tilting or pivotal disk is mounted in the valve seat. Flow in one direction causes the disk to tilt perpendicular to the seat, allowing blood flow. Pressure in the other direction presses the disk valve closed.

In another mechanical valve, a pair of flexible leaflets close the opening between the sewing ring. The leaflets are configured to flex in one direction with flow, permitting blood flow in that direction. Pressure in the opposite direction presses the leaflets together into a sealing relationship.

Bioprosthetic valves have also been utilized. For example, an aortic valve from a pig has been mounted in the sewing ring and used as a replacement mitral valve. However, this aortic valve has three leaflets; whereas, the human mitral valve has two. Further, the cross-section of the leaflets in the bioprosthetic valve is different from those in humans.

All of these valves work based on pressure differential. However, the human mitral valve operates with muscular assistance. Marginal and basal chordae extend from a lower surface of each leaflet to the papillary muscles. This muscle assists in valve operation. After a valve replacement with any of the above-discussed replacement valves, the papillary muscle no longer provides this assistance function.

The present invention overcomes the above-referenced problems and others.

SUMMARY OF THE INVENTION

In accordance with one aspect of the present invention, a replacement cardiac valve is provided. The valve includes an annular sewing ring and first and second leaflets closing a region inside of the sewing ring to define a valve. Elongated structures extend from an underside of each leaflet away from the sewing ring. The elongated structures have an attachment region adapted to be attached to a papillary muscle.

In accordance with another aspect of the present invention, a mitral valve is provided. An annular sewing ring defines an opening. A cylindrical mesh construction extends downward from the sewing ring. A pair of leaflets define a valve structure connected across the opening of the sewing ring. A synthetic basal chordae means is connected between an outer portion of each leaflet and the cylindrical mesh construction. A synthetic marginal chordae means is connected between each leaflet adjacent an inner edge of each leaflet where the leaflets meet and the synthetic basal chordae means.

In accordance with another aspect of the present invention, a method of installing a replacement heart valve which includes a sewing ring, valve leaflets, an anchoring skirt attached to the sewing ring, and a plurality of structures which mimic basal and marginal chordae connected between the leaflets and the skirt is provided. The method includes rolling or folding each skirt portion up towards the sewing ring. The sewing ring is positioned in surrounding tubular vascular structure where the replacement mitral valve is to be installed no matter the surgical removal procedure. The sewing ring is sewn into the cavity. The leaflets are opened and where the leaflets open, the skirt is unrolled or unfolded along with the chordae mimicking structures. With the leaflets still open, the chordae mimicking stuructures and the surrounding skirt are attached to papillary musculature.

One advantage of the present invention is that it mimics the human mitral valve more accurately.

Another advantage of the present invention resides in its ease of installation using conventional surgical techniques.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENTS

Figure 1:
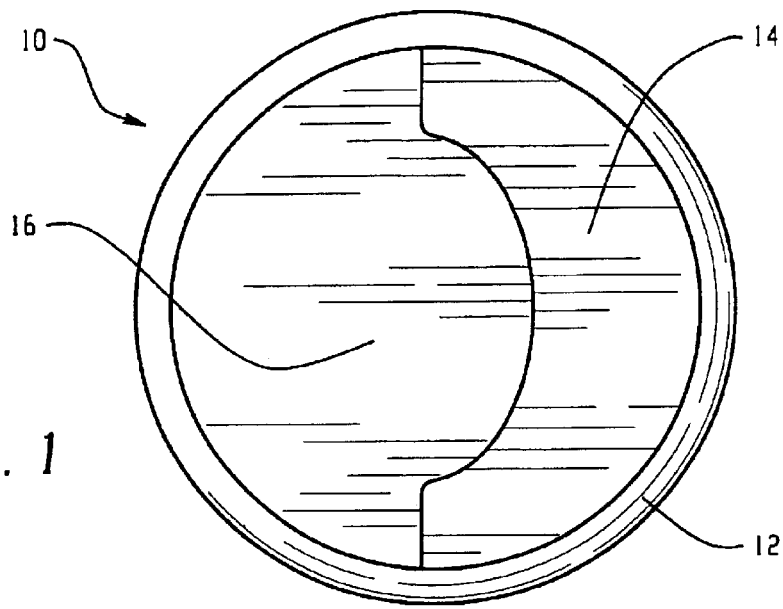
FIG. 1 is a top view of a replacement mitral valve in accordance with the present invention.

With reference to FIG. 1, a replacement mitral valve 10 includes a sewing ring 12 around its periphery. The sewing ring is of conventional construction and of a diameter sized to the patient. The sewing ring is sewn to the annular vasculature structure surrounding the location of the mitral valve to hold the replacement valve in position. A pair of leaflets 14, 16 span the opening defined by the sewing ring. The leaflets can be constructed of biologically compatible synthetic materials or of bioprosthetic materials. For example, the leaflets can be constructed from bovine pericardium.

Figure 3:
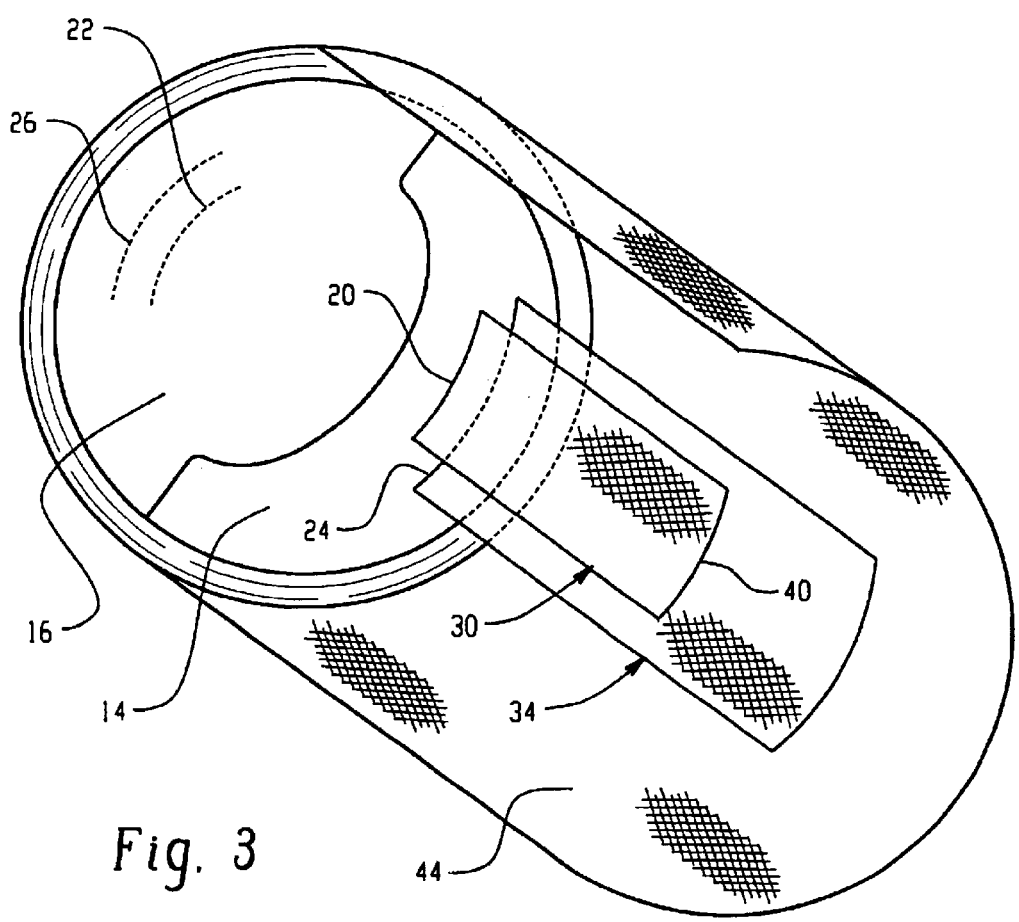
FIG. 3 is a perspective view of the valve of FIGS. 1 and 2 with the artificial chordae structure on one side of the valve removed for simplicity of illustration.
Figure 2:
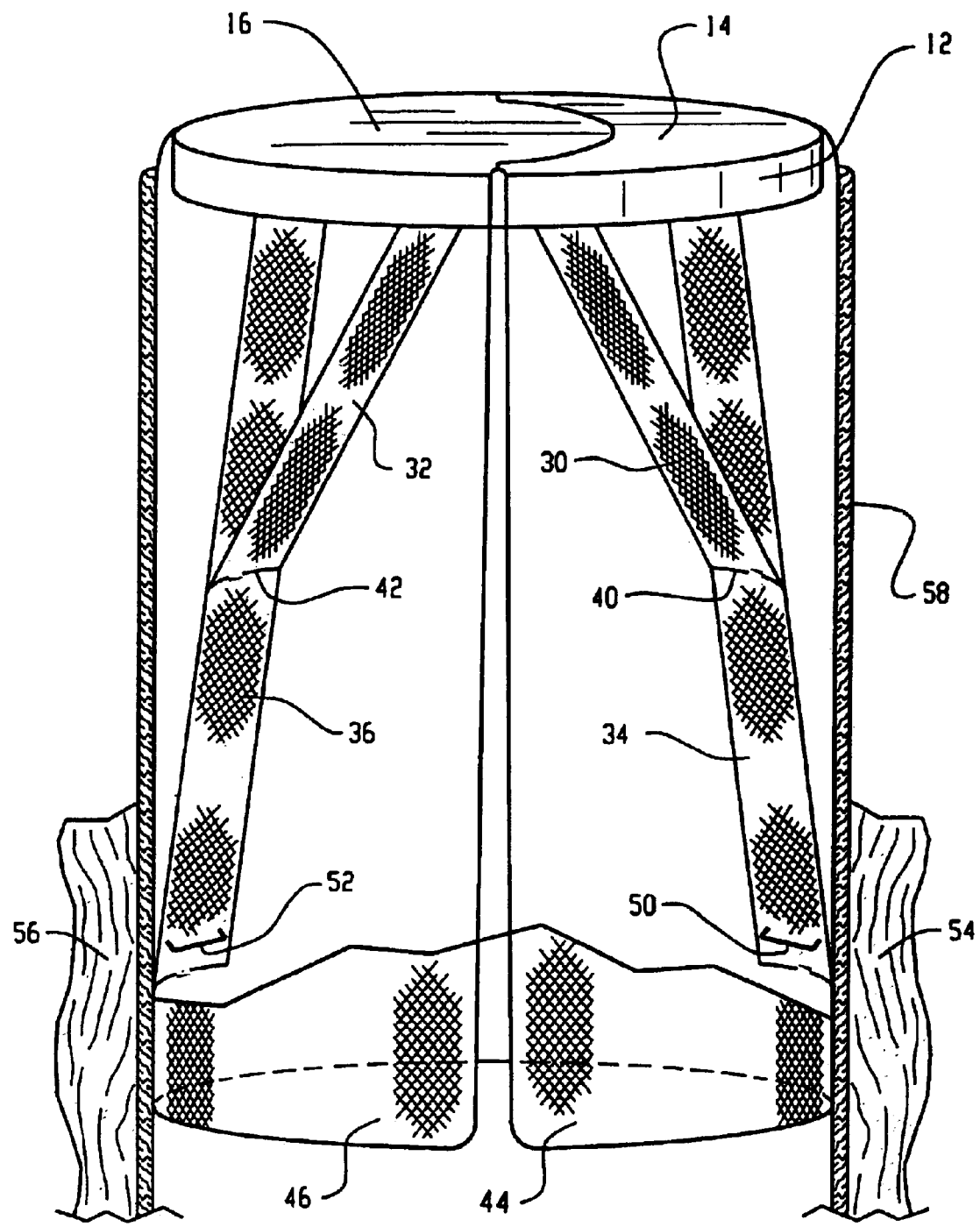
FIG. 2 is a side view of the valve of FIG. 1.

With reference to FIGS. 2 and 3, an arc 20 of inner or marginal attachment points is defined adjacent an inner edge adjacent the opening of one of the leaflets 14 and a similar arc of attachment points 22 defined on the other leaflet 16. Analogously, outer arcs 24, 26 of outer or basal attachment points are defined on each leaflet. These attachment points are selected substantially in accordance with the attachment points of the marginal and basal chordae of a healthy mitral valve.

In the illustrated embodiment, a strip of mesh or netting 30, 32 is attached along the marginal attachment points and strip of basal mesh or netting 34, 36 is attached to the leaflets along the basal attachment points. The marginal mesh or netting sections 30, 32 are attached to the basal mesh or netting sections 34 at an attachment point 40, 42 about mid-way along the basal mesh or netting section 34, 36, respectively. An anchoring skirt is defined by outer, semi-cylindrical mesh side curtains 44, 46 extend from the sewing ring along an interior of the associated vessel.

Between the attachment point 40, 42 and a terminal end of the basal mesh or strip sections, a stitch or staple 50, 52 connects the strip or mesh sections to a papillary muscle 54, 56. In this manner, contractions of the papillary muscle act through the mesh or netting sections 30, 32, 34, 36 to pull on the leaflets analogous to natural chordae.

For installation, the side curtains 44, 46 are rolled up inward, rolling the mesh strips 30, 32, 34, 36 inside. The sewing ring is positioned in a vessel 58 and stitched into place as is conventional in the mitral valve replacement surgery. The surgeon then manually opens the valve 10 and reaches through, unrolling the side curtains. The surgeon then reaches through the open valve to stitch or staple the basal mesh netting and the side curtains to the papillary muscles 54, 56. The design is compatible with any of the currently used surgical techniques for diseased mitral valves.

Figure 4:
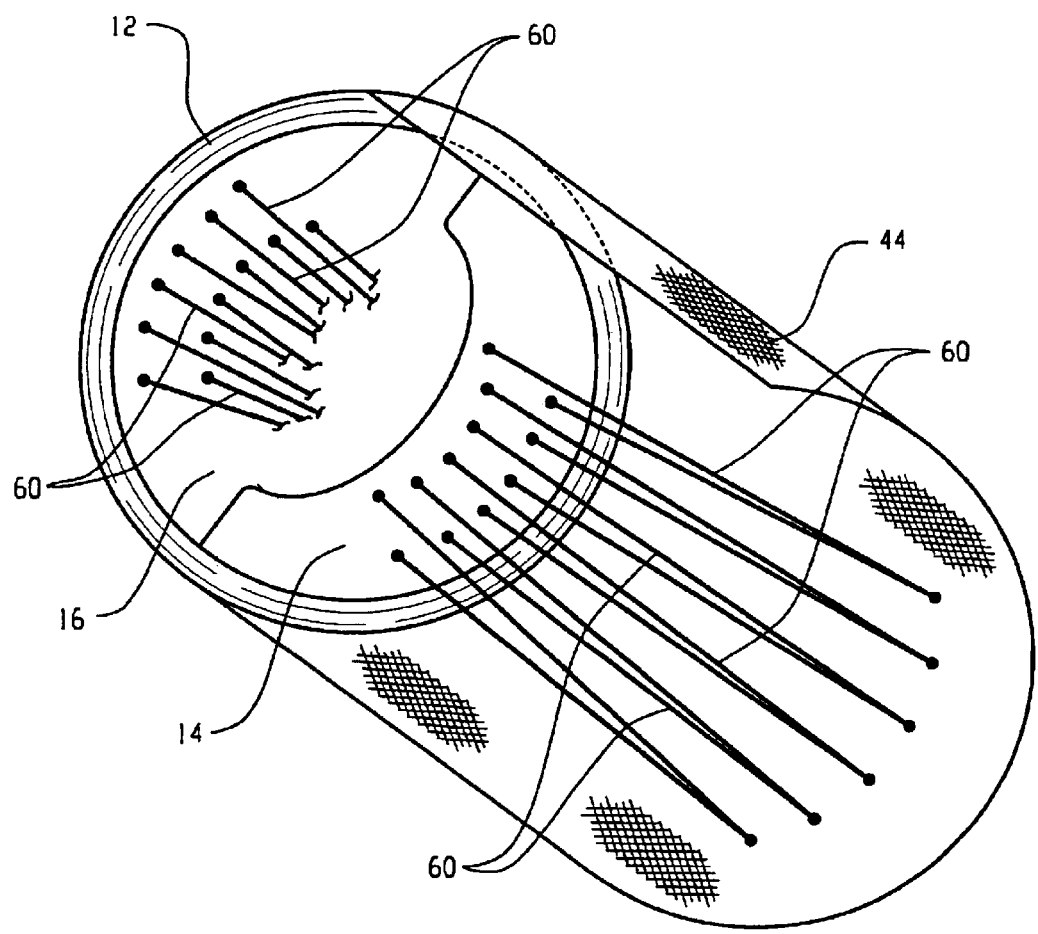
FIG. 4 is a perspective view similar to FIG. 3 of an alternate embodiment.

With reference to FIG. 4, the replacement chordae may take the form of rods or single fibers 60. As yet another alternative, bioprosthetic chordae can be utilized.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A replacement cardiac valve comprising:
    an annular sewing ring;
    first and second leaflets mounted inside the sewing ring to define a valve which is in a closed position;
    a plurality of elongated structures connected with an underside of each leaflet at a plurality of distributed points between an opening edge away from the sewing ring and the sewing ring, the elongated structures having an attachment region adapted to be attached to a papillary muscle to enable the papillary muscle to flex the leaflets open; said second elongated structures are connected to the leaflets along an arc adjacent an inner edge of each leaflet at which the leaflets meet.

2. A replacement cardiac valve comprising:
    an annular sewing ring;
    leaflets closing a region inside the sewing ring to define a valve;
    a plurality of elongated structures extending from an underside of each leaflet at a plurality of distributed points between an opening edge away from the sewing ring and having an attachment region adapted to be attached to a papillary muscle, the elongated structures being made of at least one of:
    mesh,
    netting,
    rods,
    strings, and
    fibers.

3. The valve as set forth in claim 2 wherein the plurality of elongated structures include:
    a first elongated structure extending between the underside of each leaflet and the attachment region; and
    a second elongated structure extending from the underside of each leaflet and connecting with the first elongated structure.

4. The valve as set forth in claim 2 wherein the first elongated structures are connected to each leaflet in an arc between the inner elongated structure and the sewing ring.

5. A replacement cardiac valve including:
    an annular sewing ring;
    first and second leaflets closing a region inside the sewing ring to define a valve;
    a first elongated structure extending from an underside of each leaflet away from the sewing ring and having an attachment region adapted to be attached to a papillary muscle;
    a second elongated structure extending from the underside of each leaflet and connecting with the first elongated structure; and
    a pair of semi-cylindrical mesh curtains extending downward from the sewing ring.

6. The valve as set forth in claim 5 wherein the first elongated structures are connected with the mesh curtains.

7. A replacement cardiac valve including:
    an annular sewing ring;
    first and second leaflets closing a region inside the sewing ring to define a valve;
    a first elongated structure extending from an underside of each leaflet at a plurality of distributed points between an opening edge away from the sewing ring and having an attachment region adapted to be attached to a papillary muscle;
    a mesh structure extending downward from the sewing ring.

8. The valve as set forth in claim 7 wherein the first elongated structure is connected to the mesh structure.

9. The valve as set forth in claim 8 further including:
    a second elongated structure connected between the first elongated structure at a point mid-way between the leaflet and the connection of the first elongated structure with the mesh structure, the second elongated structure further being connected with a corresponding leaflet adjacent an inner edge of the leaflet where the leaflets meet in a closed configuration.

10. A mitral valve comprising:
    an annular sewing ring which defines an opening;
    a cylindrical mesh construction extending downward from the sewing ring;
    a pair of leaflets defining a valve structure connected across the opening of the sewing ring;
    a synthetic basal chordae means connected between an outer portion of each leaflet and the cylindrical mesh construction;
    a synthetic marginal chordae means connected between each leaflet adjacent an inner edge of each leaflet where the leaflets meet and the synthetic basal chordae means.

11. The mitral valve as set forth in claim 10 wherein the cylindrical mesh construction includes a pair of semi-cylindrical sections.

12. The mitral valve as set forth in claim 10 wherein the synthetic basal and marginal chordae means include one of:
    mesh,
    netting,
    rods,
    strings,
    fibers, and
    biocompatible chords.

13. A method of installing a replacement heart valve which includes a sewing ring, valve leaflets, an anchoring skirt attached to the sewing ring, and a plurality of structures which mimic basal and marginal chordae connected between the leaflets and the skirt, the method comprising:

rolling or folding each skirt portion up toward the sewing ring;

positioning the sewing ring in a surrounding tubular vessel structure where the replacement mitral valve is to be installed;

sewing the sewing ring into the surrounding vessel structure;

opening the leaflets;

with the leaflets open, unrolling or unfolding the skirt along with the chordae mimicking structures;

with the leaflets still open, attaching the chordae mimicking structures and the surrounding skirt to papillary musculature.

* * * * *